United States Patent [19]

Boesten et al.

[11] Patent Number: 4,705,752

[45] Date of Patent: Nov. 10, 1987

[54] PROCESS FOR THE ENZYMATIC HYDROLYSIS OF D-α-AMINO-ACID AMIDES

[75] Inventors: Wilhelmus H. J. Boesten, Sittard; Maria J. H. Cals, Munstergeleen, both of Netherlands

[73] Assignee: Stamicarbon B.V., Geleen, Netherlands

[21] Appl. No.: 779,851

[22] Filed: Sep. 25, 1985

[30] Foreign Application Priority Data

Oct. 11, 1984 [NL] Netherlands ................. 8403093

[51] Int. Cl.$^4$ .................. C12P 13/04; C12P 13/08; C12P 13/06; C12N 9/78
[52] U.S. Cl. .................. 435/106; 435/115; 435/116; 435/227; 435/228; 435/253; 435/822
[58] Field of Search ........... 435/115, 116, 228, 227, 435/253, 822, 106

[56] References Cited

U.S. PATENT DOCUMENTS 4,080,259  3/1978  Boesten et al. ................. 435/228
4,211,840  7/1980  Nakamori et al. ............... 435/115
4,565,782  1/1986  Benick .......................... 435/130

FOREIGN PATENT DOCUMENTS 150854  8/1985  European Pat. Off.

OTHER PUBLICATIONS

Lechner et al., Zeitschrift fur Allgemeine Mikrobiologie 24 (1984) 8, pp. 581–584.

Primary Examiner—Charles F. Warren
Assistant Examiner—Elizabeth A. Hanley
Attorney, Agent, or Firm—Cushman, Darby & Cushman

[57] ABSTRACT

Process for the enzymatic hydrolysis of a D-α-amino-acid amide to the corresponding D-α-amino-acid, wherein an aqueous solution of the D-α-amino-acid amide is contacted with an aminoacylamidase-containing preparation obtained from a culture of Rhodococcus erythropolis or a mutant thereof and the D-α-amino-acid is subsequently recovered from the hydrolysate obtained.

8 Claims, No Drawings

PROCESS FOR THE ENZYMATIC HYDROLYSIS OF D-α-AMINO-ACID AMIDES

The invention relates to a process for the enzymatic hydrolysis of a D-α-amino-acid amide to the corresponding D-α-amino acid.

In Archives of Microbiology 138: 315–320 (1984), Springer Verlag, the effect of an enzyme with a hydrolytic activity on amide-group containing substrates is described. This enzyme originates from the microorganism Brevibacterium sp. According to U.S. Pat. No. 4,001,081, this microorganism is registered under number R 312 in the collection of the Chair of Genetics of the Ecole Nationale Agronomique in Montpellier and under number CBS 717.73 at the Centraal Bureau voor Schimmelcultures in Delft. For the substrate propionamide the highest relative specific activity 100 of the enzyme is reported. Further, this article reports a relative specific activity of 2.5 for the substrate D-α-amino-propionamide (D-alaninamide). No mention is made of a stereospecific action of the enzyme. Other D-α-amino-acid amides as substrate are not described in the above-mentioned article. The enzyme is called acetamidase, and is classified in EC 3.5.1.4 (acylamide amidohydrolase).

From J. Am. Chem. Soc. 79 p. 4538 (1957) it is known to convert D-α-amino-acid amides to the corresponding D-α-amino acids by acid or basic hydrolysis. The disadvantage of such a process consists in the occurrence of racemization and/or thermal decomposition of the desired amino acid. An additional disadvantage of the chemical hydrolysis may occur when amino acids have been formed which readily dissolve in the neutralisate of the acid or basic hydrolysis. It has been found that effective separation of the desired amino acid from the neutralized hydrolysate is extremely difficult. One way of solving this separation problem after acid or basic hydrolysis is the application of strongly basic or acid ion exchangers. Since the acids or bases used are applied in large molar excesses, correspondingly large molar amounts of expensive ion exchangers are needed.

The object of the invention is to find and apply a preparation with α-aminoacylamidasic activity (EC 3.4.11) capable of stereospecific hydrolysis of D-α-amino-acid amines to the corresponding D-α-amino-acids.

It is noted that a number of enzymes with α-aminoacylamidasic activity, also called amidasic activity, are described in Greenstein & Winitz 'Chemistry of the Amino Acid' vol. 3 pp. 1778–1781 (New York, 1961). However, these enzymes exhibit hydrolytic activity only towards α-amino-acid amides in the L-form.

The process according to the invention for enzymatic hydrolysis of a D-α-amino-acid amide is characterized in that an aqueous solution of the D-α-amino-acid amide is contacted with an aminoacylamidase-containing preparation obtained from a culture of Rhodococcus erythropolis or a mutant thereof and the D-α-amino-acid is recovered from the hydrolysate so obtained.

In this way it is achieved that the enzymatic hydrolysis of D-α-amino-acid amides proceeds stereospecifically and that the D-α-amino-acids formed can be recovered from the hydrolysate in a simple manner. Recovery may take place in a manner known as such, for example by evaporation or, on a technical scale, by spray-drying of the hydrolysis mixture obtained. In this way, ammonia formed in hydrolysis is removed from the hydrolysate and, after some time, crystals of the desired D-α-amino-acid are formed.

D-α-amino-acids can be used in the synthesis of, for example, pharmaceutical products and herbicides.

Suitable preparations with α-aminoacylamidasic activity can be won from, for example, Rhodococcus erythropolis, registered at the National Collection of Industrial Bacteria (NCIB) in Aberdeen, Scotland, under the numbers 11538, 11539 and 11540.

An especially suitable microorganism for the preparation of preparations with α-aminoacylamidasic activity according to the invention is a mutant of Rhodococcus erythropolic NCIB 11540, registered under NCIB number 12019.

Rhodococcus erythropolis can be cultured in a yeast-malt-glucose containing medium, to which, among other things, also trace elements have been added.

The enzyme with α-aminoacylamidasic activity is intracellular. For application of this enzyme whole cells can be used, whether or not freezedried. Also, the cell wall can be made permeable in the usual manner, so that the hydrolysis can proceed more efficiently. Further, it is possible to use a cell-free extract. If desired, the enzyme can be recovered in purified form from the cell-free extract in a known manner. In the above-mentioned applications of the enzyme, use can be made of known immobilization techniques, such as described in, for example, 'Applied Biochemistry and Bioengineering' Vol. 1 (1976) and Vol. 4 (1983), Academic Press. When the microorganism or the purified enzyme is used in immobilized form, the recovery of the biocatalyst relatively simple, for example by filtration.

The hydrolysis can be conducted at a temperature of between 0° and 60° C., preferably between 20° and 45° C., and at a pH of between 6 and 10, since under these conditions the hydrolysis proceeds the most quickly.

The duration of the hydrolysis may vary from, for example 1 to 24 hours.

As substrate, preferably Dα-amino-acid amines with 3–6 C-atoms are used, more in particular D-alaninamide, D-valinamide, D-aminobutyric amide, D-leucinamide, D-serinamide and D-threoninamide.

The invention will be explained with the following examples.

EXAMPLES

The microorganisms used for the invention were obtained from earth and waste samples by enrichment. The following properties were determined:

Morphology:

The primary mycelium soon separates into rods and cocs on GYEA (Glucose-Yeast-Extract-Agar). The colonies on GYEA and Sauton's agar are irregular in shape and orange-red in colour. The microorganism is aerobic, immobile and partially acid-resistant and has no endospores.

Temperature requirement
Growth at 4°–40° C. Optimum 30° C.

Enzymatic activity
Urease, phosphatase, catalase, nitrate reduction, nitrilase positive. In addition, the inventors have found that the microorganism also has aminoacylamidase activity.

Degradation test
Adenine (0.5% weight/volume (w/v)) ad L-tyrosine (0.5% w/v) positive.

Fermentation studies:

There is formation of acid from glycerol, sorbitol, trehalose and sucrose, but not from adonitol, arabinose, cellobiose, galactose, glycogen, inuline, melezitose, rhamnose or xylose.

Sole C-source (1% w/v):

There is growth on glucose, glycerol, meso-inositol, sorbitol, trehalose, inuline, maltose, mannitol, adipate, gluconate, lactate, maleate, pyruvate, sebacic acid, succinate and testosterone but not on glycogen, inositol, rhamnose, benzamide, m-OH-benzoic acid, malonate or tartrate as the sole C-source for energy and growth.

Sole C and N-source

There is no growth on serine or trimethylene diamine.

Growth in the presence of:

Crystal violet (1 ppm w/v) and sodium azide (0.02% w/v) positive.

Lipide properties:

The microorganism has free mycolinic acids with 36–48 C-atoms, and has menaquinones with 8 isoprene units and one hydrogenated double bond. There are no mycobactines or nocobactines.

G+C composition of the DNA:

G+C is 61–67 mole percent at $T_m$.

Occurrence:

In earth and waste.

On the basis of the above-described characteristics, the isolated strains belong to the genus Rhodococcus, and more spcifically to the species *Rhodococcus erythropolis* in the sense of M. Goodfellow and G. Alderson (J. Gen. Microbiol. 100 (1977); 99–122). Isolated strains are registered at NCIB under the number NCIB 11538, 11539 and 11540.

A mutant strain of *Rhodococcus erythropolis* NCIB 11540 with a higher aminoacylamidasic activity was obtained by mutagenesis. To this end, a crystal of N-methyl-N'-nitro-N-nitrosoguanidine (NMG) was placed at the centre of a grafted plate (Yeast-carbon based medium with 0.78 g of KNO3 per 100 mL plus 1.5% agar) and was incubated for 6 days at 30° C. The colonies from this plate were tested for the same characteristics as described for the wild type. The mutant had the same characteristics as the wild type NCIB 11540, but had a markedly higher aminoacylamidasic activity. This mutant is registered at the NCIB under number 12019.

Preparation of a culture of *Rhodococcus erythropolis* NCIB 11540.

The microorganisms used in the invention are preserved on inclined tubes at 10° C. on a so-called yeast-carbon based (Difco) agar medium, to which per 100 mL 0.78 g of KNO3 has been added.

From the above-mentioned medium with microorganisms, a preculture of 200 mL was planted on the same medium but without agar. This was then incubated for 72 hours at 30° C. The pH of the medium was 7.2.

A ten-liter chemap fermentor was filled as follows:

(1) 50 grams of yeast extract in 2 liters of distilled water (pH 7.2) were sterilized for 20 minutes at 120° C. and then cooled.

(2) 8 liters of distilled water with 100 grams of malt extract, 80 grams of bactopeptone, 5 grams of KNO3, 40 grams of glucose and 10 mL of trace elements ('Huntners metals') were added. The ultimate pH was 7.2. The total contents were then sterilized anew for 30 minutes, at 110° C.

(3) the total pre-culture was added.

(4) Acetonitrile (0.2% w/v) was added under sterile conditions.

The fermentor culture was now kept at a constant pH of 7.2 for 40 hours, at 30° C. The wet-cell yield after cultivation was about 270 g. From these cells, a cell suspension was made in a Sörensen phosphate buffer (pH 7.2) to which 70 vol. % glycerol had been added, and the whole was stored at −20° C.

Example I

After centrifugation of the glycerol cell suspension, the cells were washed with phosphate buffer of pH 7.,2 (Sörensen) and then centrifugated again. Of strain NCIB 11540 of *Rhodococcus erythropolis*, 200 mg of wet cells were added to 5 mL of a 20.0 wt. % solution of D-valinamide in phosphate buffer of pH 7.2 (Sörensen). For 60 minutes, incubation took place in a thermostatted reaction vessel at 30° C. The pH of the reaction (pH 7.2) hardly changed. After the reaction time had elapsed, 1.0 g was taken from the reaction mixture and was added to 100 mL of distilled water. After addition of 1 mL of 10N NaOH the amount of ammonia formed was measured with the aid of an Orion ammonia-selective electrode.

The amidasic activity, expressed in the amount of ammonia formed, is equivalent to the amount of substrate converted and was 90 units (micromoles per minute) per gram of dry substance.

Example II

Washed cells of the mutant strain NCIB 12019 of *Rhodococcus erythropolis* were tested as in Example I. The amidasic activity in the conversion of D-valinamide in this mutant was 250 units (micromoles per minute) per gram of dry substance.

Example III 200 g of an aqueous solution containing 4.0 wt. % D-valinamide (specific rotation $[\alpha]_D = -11.5°$ (c=2.0; $H_2O$)) was stirred for 15 minutes at room temperature with 10 g of centrifugated and washed cells of *Rhodococcus erythropolis* NCIB 11540.

Next, the cells were centrifugated, washed with water and centrifugated again. The aqueous layers were combined, decoloured with 0.5 g of activated carbon at 50° C. and evaporated under vacuum at 40° C. The residue was dried further in a vacuum drying oven at 40° C.

The yield of pure D-valine (determined by thin layer chromatography (TLC)) was 7.6 g. The yield was 95%.

D-valine: $[\alpha]_D = -28.0°$ (C=8.0; 6N HCl).

Example IV 10 grams of cells of *Rhodococcus erythropolis* NCIB 11540 were immobilized in calcium alginate and the spherules so obtained were stirred at room temperature with 250 g of a 5.0 wt. % aqueous solution of D-alaninamide ($[\alpha]_D = -7.1°$ (C=2.0; $H_2O$)).

After 24 hours, the alginate spherules were filtered off and washed with water. The two aqueous layers were combined and then worked up as described in Example III.

The amount of pure D-alanine obtained (determined by TLC) was 11.9 g (yield=95.2%).

The specific rotation was $[\alpha]_D = -14.8°$ (C=10; 6N HCl).

Example V 5 grams of cells of *Rhodococcus erythropolis* NCIB 11540 immobilized on sand were introduced into a column, after which 300 grams of a 2.5 wt % aqueous solution of D-leucinamide ($[\alpha]_D = -7.5°$ (C=2.0; H$_2$O)) were circulated through the column for 20 hours at room temperature.

Afterwards, no more starting product was present in the solution, according to a TLC determination. After a working-up procedure as described in Example III, 7.0 g (yield=93.3%) of pure D-leucine (TLC-determined) was obtained.

$[\alpha]_D = -15.0°$ (C=4.0; 6N HCl).

Comparative example

To a solution of 11.6 grams (0.1 moles) of D-valinamide in 36 mL of water, 20 mL of 96 wt. % sulphuric acid was added with stirring, after which the solution was for 4 hours heated (100° C.) while being stirred. After cooling to 40° C., the acid hydrolysis mixture was neutralized to an acidity of pH=5.0 with 50 mL of 25 wt. % ammonia while being stirred and cooled. After neutralization, the ammonium sulphate content of the aqueous solution was 40 wt. %.

The crystalline D-valine so formed was isolated by filtration over a glass filter at 40° C. (wash liquid: 3×5 mL of water and 3×5 mL of acetone).

The D-valine yield (TLC-pure; sulphate-free) after drying (0.016 bar; 50° C.; 8 hours) was 7.9 grams (yield 67.5%). Specific rotation of D-valine: $[\alpha]_D = -27.9°$ C. (C=8.0; 6N HCl).

According to a TLC determination, more than 99% of the D-valine amide had been hydrolyzed to D-valine.

We claim:

1. A process for the enzymatic hydrolysis of a D-α-amino-acid amide to the corresponding D-α-amino-acid, wherein an aqueous solution of the D-α-amino-acid amide is contacted with an aminoacylamidase-containing preparation obtained from a culture of *Rhodococcus erythropolis* or a mutant thereof and the D-α-amino-acid is subsequently recovered from the obtained hydrolysate.

2. A process according to claim 1, wherein the hydrolysis is conducted at a pH of 6–10 and at a temperature of 20°–45° C.

3. A process according to claim 1, wherein *Rhodococcus erythropolis* or a mutant thereof is used in the form of wet cells.

4. A process according to claim 1, wherein use is made of *Rhodococcus erythropolis* or a mutant thereof immobilized on a suitable carrier.

5. A process according to claim 1, wherein use is made of *Rhodococcus erythropolis* as registered under NCIB number 11538, 11539 or 11540.

6. A process according to claim 1, wherein use is made of a mutant of *Rhodococcus erythropolis* registered under NCIB number 12019.

7. A process according to claim 1, wherein a D-α-amino-acid amide with 3–6 carbon atoms is used as the starting compound.

8. A process according to claim 1, wherein as D-α-amino-acid amide use is made of D-alaninamide, D-valinamide, D-aminobutyric amide, D-leucinamide, D-serinamide or D-threoninamide.

* * * * *